United States Patent [19]

Gauthier-Fournier

[11] Patent Number: 5,529,713
[45] Date of Patent: Jun. 25, 1996

[54] CLEANING AND DISINFECTANT COMPOSITIONS FOR HOUSEHOLD USE POSSESSING HYPOALLERGENIC PROPERTIES AND ACARICIDAL CAPABILITIES

[75] Inventor: François Gauthier-Fournier, Meze, France

[73] Assignee: EPARCO, Paris, France

[21] Appl. No.: 700,487

[22] Filed: May 15, 1991

[30] Foreign Application Priority Data

May 15, 1990 [FR] France ................................. 90 06039

[51] Int. Cl.$^6$ ..................................................... C11D 3/48
[52] U.S. Cl. ........................... 252/106; 252/107; 252/173
[58] Field of Search ....................... 252/106, 107, 252/173

[56] References Cited

U.S. PATENT DOCUMENTS

| | | |
|---|---|---|
| 3,326,808 | 6/1967 | Noseworthy .......................... 252/106 |
| 3,954,644 | 5/1976 | Krezanoski et al. ..................... 252/106 |
| 4,576,729 | 3/1986 | Paszek et al. ........................... 252/106 |
| 4,666,940 | 5/1987 | Bischoff et al. ........................ 514/544 |
| 4,714,563 | 12/1987 | Kajs et al. .............................. 252/107 |
| 4,800,037 | 1/1989 | Mazzola ................................. 252/109 |
| 5,000,867 | 3/1991 | Heinhuis-Walther et al. ......... 252/106 |
| 5,139,705 | 8/1992 | Wittpenn, Jr. et al. ................. 252/547 |

OTHER PUBLICATIONS

Grant and Hackh's Chemical Dictionary, 5th edition, McGraw-Hill Book Company 1987 p. 72.

*Primary Examiner*—Gary P. Straub
*Assistant Examiner*—Timothy C. Vanoy
*Attorney, Agent, or Firm*—Barry Evans; Curtis Morris & Safford

[57] ABSTRACT

A cleaning and disinfecting composition for household use comprising ethoxylated fatty alcohol; co-surfactant; isopropyl alcohol; polyhexamethylene biguanide hydrochloride; didecyldimethylammonium chloride and benzalkonium chloride.

25 Claims, No Drawings

CLEANING AND DISINFECTANT COMPOSITIONS FOR HOUSEHOLD USE POSSESSING HYPOALLERGENIC PROPERTIES AND ACARICIDAL CAPABILITIES

FIELD OF THE INVENTION

The invention relates to cleaning and disinfectant compositions for household use possessing hypo-allergenic properties and acaricidal capabilities.

PRIOR ART

The cleaning and disinfectant compositions for surfaces or liquids such as walls, inner surfaces of vessels, sinks, tables, worktops, and the like have composition characteristics which are generally determined by their conditions of use. Cleaning and disinfectant compositions for individual or collective household use as well as those for industrial use are more particularly known. The compositions for household use must satisfy the requirements of cost price and safety in particular. Commercially known compositions for household use are most often based on javel water. When necessary, the composition is provided for sale in the concentrated form and used in the water-diluted form. Nevertheless, the disinfectant efficacy of such compositions turns out to be particularly low especially in the dilute form. Furthermore, they exhibit other disadvantages (safety, odor and the like). The compositions for industrial use generally require a higher efficacy with a possibly higher price in consequence. For example such a known composition for industrial use comprises a non-ionic surface-active agent, butyl glycol, by way of surface-active agent and polyhexamethylene biguanide hydrochloride—such as the one known under the name VANTOCIL IB from the company I.C.I.—by way of biocide. However, on the one hand, the disinfectant efficacy of such compositions is also limited and, on the other hand, these compositions cannot be employed for household use.

Moreover, the following documents may be referred to: EP-243 713 which relates to a bactericidal composition comprising didecyldimethylammonium chloride by way of biocide; UK-2 132 087 which relates to a composition comprising benzalkonium chloride and quaternary ammonium compounds; JP-82 109899 which relates to a composition comprising a non-ionic surface-active agent; JP-82 09717; U.S. Pat. No. 4,272,395; UK-1 562 961; UK-1 551 224; DE-2 810 998; DE-2 226 823; DE-1 923 889; FR-69 04494; FR-71 11177; FR-74 00681; FR-74 16119; FR-78 31058; FR-78 27929; U.S. Pat. No. 4,540,505; UK-795 814; DE-2 811 756; FR-1 576 016; DE-3 639 635; WO-86 05 509; EP-99 209; WO-86 02 090.

Moreover, French regulations on cleaning and disinfectant compositions for household use does not allow the use of some products or compounds as components which make up the composition.

The AFNOR NFT 72171 standard makes it possible to simulate the simultaneous cleaning and disinfectant conditions when the presence of organic materials adversely affects the disinfectant activity. In the case of the implementation of the standard with 1% albumin and 1% yeast extract as "interfering substance" in the presence of qualitatively and quantitatively known bacteria and javel water of desired concentration, the decline in the number of microorganisms, determined after five minutes, does not reach the threshold established by the standard in order to acquire the designation of "disinfectant product". The invention relates to compositions which, contrary to Javel water, can acquire this AFNOR designation of "bactericidal disinfectant".

The aim of the invention therefore is to propose cleaning and disinfectant compositions for household use with an efficacy, biocidal in particular, which is very substantially higher than that of compositions for household use known to this date and, simultaneously, satisfying the regulatory, commercial and practical usage requirements which these compositions must satisfy. The aim of the invention furthermore is for such compositions to be provided for sale in the concentrated form and used in the dilute form without this dilution substantially affecting the properties, biocidal in particular, of the compositions, but achieving the opposite on the contrary. Finally the aims of the invention are that the composition should acquire the quality of "disinfectant" according to the aforementioned AFNOR NFT 72171 standard, exhibit hypoallergenic properties and possess acaricidal capabilities.

SUMMARY OF THE INVENTION

To this end, the invention proposes firstly a cleaning and disinfectant composition for household use, which comprises, in combination, ethoxylated fatty alcohol, a co-surface-active agent, isopropyl alcohol, polyhexamethylene biguanide hydrochloride, didecyldimethylammonium chloride and benzalkonium chloride.

The invention therefore relates to a cleaning and disinfectant composition for individual or collective household use. In this capacity, this composition satisfies the requirements imposed by such a usage: reasonable cost price, ensured safety and compliance with current regulations.

The composition which is now described is mainly intended to be provided in concentrated form with the advantages which derive from such a presentation, this concentrated composition being diluted with water for its effective use.

Such a cleaning and disinfectant composition is intended for cleaning and disinfecting surfaces or liquids, in the home, for various applications or supports: walls, inner surfaces of vessels, sinks, tables, worktops, and the like, kitchens, bathrooms, toilets or the like.

The composition according to the invention comprises in combination at least one non-ionic surface-active agent, at least one co-surface-active agent chosen from the group comprising dipropylene glycol methyl ether and isopropyl alcohol and, finally, at least one cationic biocide comprising benzalkonium chloride or/and its equivalent. Furthermore, this composition comprises in addition water which forms the solvent, including in its concentrated form, and finally, when necessary, at least one colorant and/or perfume.

The non-ionic surface-active agent or at least one of the non-ionic surface-active agents or the non-ionic surface-active agents used in the composition is a fatty alcohol with a branched or unbranched alkyl chain with at least one and up to eleven moles of ethylene oxide. Thus, the composition considered comprises as non-ionic surface-active agent a 7-EO fatty alcohol combined with a 3-EO fatty alcohol, the assays carried out having demonstrated that such a combination gave particularly efficacious and surprising results. When necessary, an ethoxylated alcohol (non-ionic surface-active agent) additionally comprises between 1 and 10 propylene oxides (inclusive).

A co-surface-active agent is chosen from the group comprising dipropylene glycol methyl ether and isopropyl alcohol. Furthermore, this group totally excludes butyl glycol.

A cationic biocide is chosen from the group comprising in addition to benzalkonium chloride or/and its equivalent, polyhexamethylene biguanide hydrochloride and didecyldimethylammonium chloride. In particular, there is used as cationic biocide the combination of benzalkonium chloride or/and its equivalent, of a polyhexamethylene biguanide hydrochloride and of didecyldimethylammonium chloride.

For example, a benzalkonium chloride equivalent is chosen from the group comprising quaternary ammonium chlorides or bromides having a linear or branched saturated hydrocarbon chain with 8 to 18 carbon atoms (inclusive) and whose aryl radical corresponds to the phenyl group or to the benzyl group. There may be mentioned the chlorides or bromides of:

alkyltrimethylammonium dialkyldimethylammonium trialkylmethylammonium alkylaryldimethylammonium alkyl(ethylaryl)dimethylammonium dialkylarylmethylammonium trialkylarylammonium alkyldiarylmethylammonium dialkyldiarylammonium alkyldimethylaryl[phenoxy (or cresoxy)ethoxyethyl]ammonium alkylbenzylimidazolinium as well as the chloride (but not the bromide) of alkylpyridinium.

The proportions or the proportion ratios of the various components of the composition will now be given. It is understood that these proportions or ratios are expressed by weight, this precision no longer being given hereafter.

The composition such as just described, in the concentrated form, may comprise up to 96% of water, in particular of the order of 42.4%.

It may comprise between 1% and 50% of surface-active agents (one or more surface-active agents), in particular of the order of 22.5% for the surface-active agents taken as a whole.

It may furthermore comprise 1% to 25% of co-surface-active agents, in particular of the order of 14%.

Finally, it may comprise between 1% and 40% of cationic biocide, in particular of the order of 20.1%.

The ratio of 7-EO fatty alcohol relative to 3-EO fatty alcohol is between 1.5 and 40 in particular and of the order of 10.25. The ratio of isopropyl alcohol relative to dipropylene glycol methyl ether is between 0.33 and 3 in particular and of the order of 1. Finally the ratios of didecyldimethylammonium chloride and benzalkonium chloride or/and its equivalent relative to polyhexamethylene biguanide hydrochloride are between 0.1 and 20, and in particular are of the order of 1.18 and 1.76 respectively.

Excellent results have been obtained with a cleaning and disinfectant composition which comprises of the order of 20.5% 7-EO fatty alcohol, of the order of 2% 3-EO fatty alcohol, of the order of 7% dipropylene glycol methyl ether, of the order of 7% isopropyl alcohol, of the order of 5.1% polyhexamethylene biguanide hydrochloride, of the order of 6% didecyldimethylammonium chloride and of the order of 9% benzalkonium chloride or/and its equivalent.

For example and in compliance with a possible embodiment of the invention, there may be used as fatty alcohol the polyethoxylated-fatty alcohols marketed by the company I.C.I. FRANCE under the names SYMPERONIC A 7 and SYMPERONIC A 3.

The co-surface-active agent consisting of dipropylene glycol methyl ether may be for example DOWANOL DPM from DOW CHEMICAL.

The biocide consisting of polyhexamethylene biguanide hydrochloride may be at a concentration of 20% and be composed of VANTOCIL IB from the company I.C.I. FRANCE. As for didecyldimethylammonium chloride, it may be at 50% and consist of BARDAC 22 from the company LONZA FRANCE. In the case of benzalkonium chloride, it may be at 50% and consist of VITALUB QC 50 from the company VALLUY.

Naturally, variant compositions which could enter the scope of the present invention may be envisaged. Such would be the case for compositions whose components would be strictly equivalent to those described or very similar. In particular, and in the case of surface-active agents, fatty alcohols having an ethoxylation number different from those—3 and 7 —mentioned may be used. For example this ethoxylation number may be between 1.5 and 11.

Such a composition as just described may thus be provided in concentrated form with the advantages which derive from such a presentation and be diluted with water for use. For example, the dilution may be as much as 8 g of the composition per liter, the degree of dilution depends in particular on the use envisaged for the composition.

What is claimed is:

1. A cleaning and disinfecting composition for household use, comprising, in combination, ethoxylated fatty alcohol; a co-surfactant; isopropyl alcohol; polyhexamethylene biguanide hydrochloride; didecyldimethylammonium chloride; and benzalkonium chloride.

2. The composition according to claim 1, further comprising a solvent.

3. The composition according to claim 2, further comprising water as the solvent.

4. The composition according to claim 3, wherein water is present in the amount of about 42.4% by weight.

5. The composition according to claim 1, further comprising at least one colorant.

6. The composition according to claim 5, further comprising at least one perfume.

7. The composition according to claim 1, further comprising at least one perfume.

8. The composition according to claim 1, wherein the ethoxylated fatty alcohol contains at least one propylene oxide.

9. The composition according to claim 1, wherein the benzalkonium chloride is at least partially replaced by a compound chosen from the group consisting of quaternary ammonium chlorides and bromides having a straight-chain or branched saturated hydrocarbon chain with 8 to 18 carbons, and wherein the aryl radical corresponds to the phenyl group or to the benzyl group, with the exception of alkylpyridinium bromide.

10. The composition according to claim 1 wherein the ethoxylated fatty alcohol is a combination of a first ethoxylated fatty alcohol having an ethoxylation number of 7 and a second ethoxylated fatty alcohol having an ethoxylation number of 3.

11. The composition according to claim 10, wherein the ratio, by weight, of the first ethoxylated fatty alcohol to the second ethoxylated fatty alcohol is from about 1.5 to 40.

12. The composition according to claim 11, wherein the ratio of the first ethoxylated fatty alcohol to the second ethoxylated fatty alcohol is about 10.25.

13. The composition according to claim 1, wherein the cosurfactant is dipropylene glycol methyl ether and which excludes butyl glycol.

14. The composition according to claim 1, wherein the fatty alcohol is present in an amount of about 1% to 50% by weight.

15. The composition according to claim 14, wherein the ethoxylated fatty alcohol is present in an amount of about 22.5% by weight.

16. The composition according to claim 1, wherein the isopropyl alcohol is present in an amount of about 1% to 25% by weight.

17. The composition according to claim 1, wherein the polyhexamethylene biguanide hydrochloride, didecyldimethylammonium chloride and benzalkonium chloride together are present in an amount of about 1% to 40% by weight.

18. The composition according to claim 1, wherein the ratio, by weight of isopropyl alcohol to dipropylene glycol methyl ether is from about 0.33 to 3.

19. The composition according to claim 18, wherein the ratio of isopropyl alcohol to dipropylene glycol methyl ether is about 1.

20. The composition according to claim 1, wherein the ratio by weight of didecyldimethylammonium chloride and benzalkonium chloride to polyhexamethylene biguanide hydrochloride is from about 0.1 to 20.

21. The composition according to claim 20, wherein the ratios by weight of didecyldimethylammonium chloride and benzalkonium chloride to polyhexamethylene biguanide hydrochloride is from about 1.18 to 1.76.

22. The composition according to claim 1, which comprises by weight, about 20.5% of ethoxylated fatty alcohol having an ethoxylation number of 7; about 2% of ethoxylated fatty alcohol having an ethoxylation number of 3; about 7% of dipropylene glycol methyl ether; about 7% of isopropyl alcohol; about 5.1 of polyhexamethylene biguanide hydrochloride; about 6% of didecyldimethylammonium chloride; about 9% of benzalkonium chloride.

23. The composition according to claim 1, which is prepared in concentrated form and which may be diluted with water for use.

24. The composition according to claim 23, which is diluted with water to approximately 8 g per liter for use.

25. A cleaning and disinfecting composition for household use, comprising, in combination, about 1 to 50 percent by weight of ethoxylated fatty alcohol; about 1 to 25 percent by weight of a co-surfactant; about 1 to 25 percent by weight of isopropyl alcohol; polyhexamethylene biguanide hydrochloride; didecyldimethylammonium chloride; and benzalkonium chloride, wherein the polyhexamethylene biguanide hydrochloride, didecyldimethylammonium chloride and benzalkonium chloride together are present in an amount of about 1 to 40 percent by weight.

* * * * *